United States Patent
Washington, Sr. et al.

(10) Patent No.: US 11,065,162 B2
(45) Date of Patent: Jul. 20, 2021

(54) AMPUTATED LEG MEDICAL WRAP APPARATUS

(71) Applicants: Joe Washington, Sr., Thornville, OH (US); Ruie Harris, Thornville, OH (US)

(72) Inventors: Joe Washington, Sr., Thornville, OH (US); Ruie Harris, Thornville, OH (US)

(*) Notice: Subject to any disclaimer, the term of this patent is extended or adjusted under 35 U.S.C. 154(b) by 275 days.

(21) Appl. No.: 16/400,421

(22) Filed: May 1, 2019

(65) Prior Publication Data

US 2020/0345564 A1 Nov. 5, 2020

(51) Int. Cl.
  *A61F 13/00* (2006.01)
  *A61F 13/82* (2006.01)
  *A61F 13/06* (2006.01)

(52) U.S. Cl.
  CPC .............. *A61F 13/82* (2013.01); *A61F 13/06* (2013.01)

(58) Field of Classification Search
  CPC .. A61F 2/64; A61F 2/80; A61F 2/7812; A61F 2002/608; A61F 2002/7817; A61F 2002/7862; A61F 2002/7893; A61F 2002/7881; A61F 2002/5007; A61F 13/00029; A61F 13/10; A61F 13/45; A61F 13/12; A61F 13/06; A61F 13/03; A61F 13/82; A61F 2230/0017; A61F 2230/0026; A61F 2230/0069; A61F 2230/0019; A61F 2230/0067; A61F 2230/0018

USPC ............................................. D24/190
  See application file for complete search history.

(56) References Cited

U.S. PATENT DOCUMENTS

| | | | | |
|---|---|---|---|---|
| 3,032,035 A | * | 5/1962 | Dempsey | A61F 2/78 602/61 |
| 3,138,156 A | * | 6/1964 | Crowell | A61F 2/7812 602/61 |
| 4,644,946 A | | 2/1987 | Cremona-Bonato | |
| 5,507,722 A | * | 4/1996 | Richardson | A61F 2/7812 602/60 |
| 7,575,561 B2 | * | 8/2009 | Smith | A61F 13/06 602/60 |
| 8,827,941 B2 | * | 9/2014 | Davis | A61F 5/0102 602/62 |
| 8,945,237 B2 | * | 2/2015 | Cornell | A61F 2/78 623/33 |
| 2005/0278039 A1 | * | 12/2005 | Nobbe | A61F 2/7812 623/31 |
| 2011/0201985 A1 | * | 8/2011 | Entler | A61D 9/00 602/62 |

(Continued)

*Primary Examiner* — Kim M Lewis

(57) ABSTRACT

An amputated leg medical wrap apparatus for securing and maintaining bandages on an amputated leg stump includes a bottom pad. A pair of straps comprises a top strap and a bottom strap each coupled to a bottom outer surface of the bottom pad. A pair of top pads comprises a right top pad and a left top pad coupled to the top strap and the bottom strap. The right top pad has a first hook-and-loop fastener coupled to a top inner surface and the left top pad has a second hook-and-loop fastener coupled to a top outer surface to secure the apparatus to a user's amputated leg stump. A belt strap is coupled to the bottom outer surface of the bottom pad and has a right belt strap extension and a left belt strap extension each having a looped top end configured to receive a waist belt.

9 Claims, 5 Drawing Sheets

(56) References Cited

U.S. PATENT DOCUMENTS

| | | | |
|---|---|---|---|
| 2013/0267882 A1* | 10/2013 | Volker | A61F 15/006 602/79 |
| 2016/0058634 A1* | 3/2016 | Wagner | A61F 15/004 602/12 |
| 2016/0074178 A1* | 3/2016 | Phillips | A61F 2/76 264/222 |
| 2018/0185175 A1* | 7/2018 | Whiteside | A61F 2/60 |
| 2020/0170810 A1* | 6/2020 | Donovan | A61F 5/3715 |

* cited by examiner

AMPUTATED LEG MEDICAL WRAP APPARATUS

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION

(1) Field of the Invention

(2) Description of Related Art Including Information Disclosed Under 37 CFR 1.97 and 1.98

The disclosure and prior art relates to medical wraps and more particularly pertains to a new medical wrap for securing and maintaining bandages on an amputated leg stump.

BRIEF SUMMARY OF THE INVENTION

An embodiment of the disclosure meets the needs presented above by generally comprising a bottom pad having a bottom inner surface, a bottom outer surface, a back portion, a bottom portion, a right side portion, and a left side portion. A pair of straps is coupled to the bottom pad. The pair of straps comprises a top strap and a bottom strap each coupled to the bottom outer surface and having a right extension and a left extension. A pair of top pads is coupled to the pair of straps. The pair of top pads comprises a right top pad and a left top pad each having a top inner surface and a top outer surface. The right top pad and the left top pad are coupled to the right extension and the left extension, respectively, of the top strap and the bottom strap. The right top pad has a first hook-and-loop fastener coupled to the top inner surface and the left top pad has a second hook-and-loop fastener coupled to the top outer surface. The first and second hook-and-loop fasteners are selectively engageable and are configured to secure the apparatus to a user's amputated leg stump. A belt strap is coupled to the bottom outer surface of the bottom pad and comprises a right belt strap extension and a left belt strap extension each having a looped top end extending past an upper edge of the bottom pad. The looped top end of each of the right belt strap extension and the left belt strap extension is configured to receive a waist belt.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
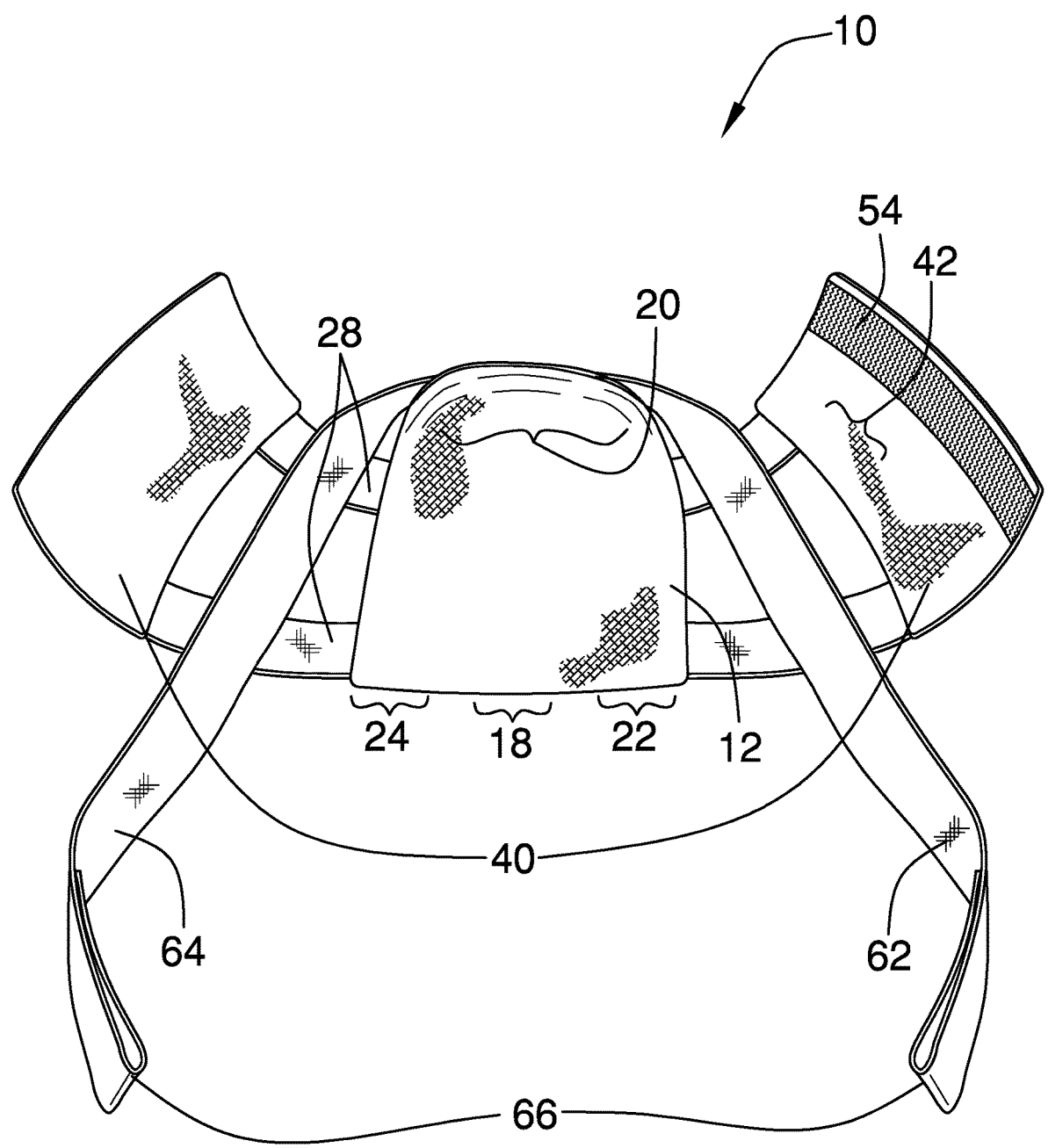
FIG. 1 is an isometric view of an amputated leg medical wrap apparatus according to an embodiment of the disclosure.
Figure 2:
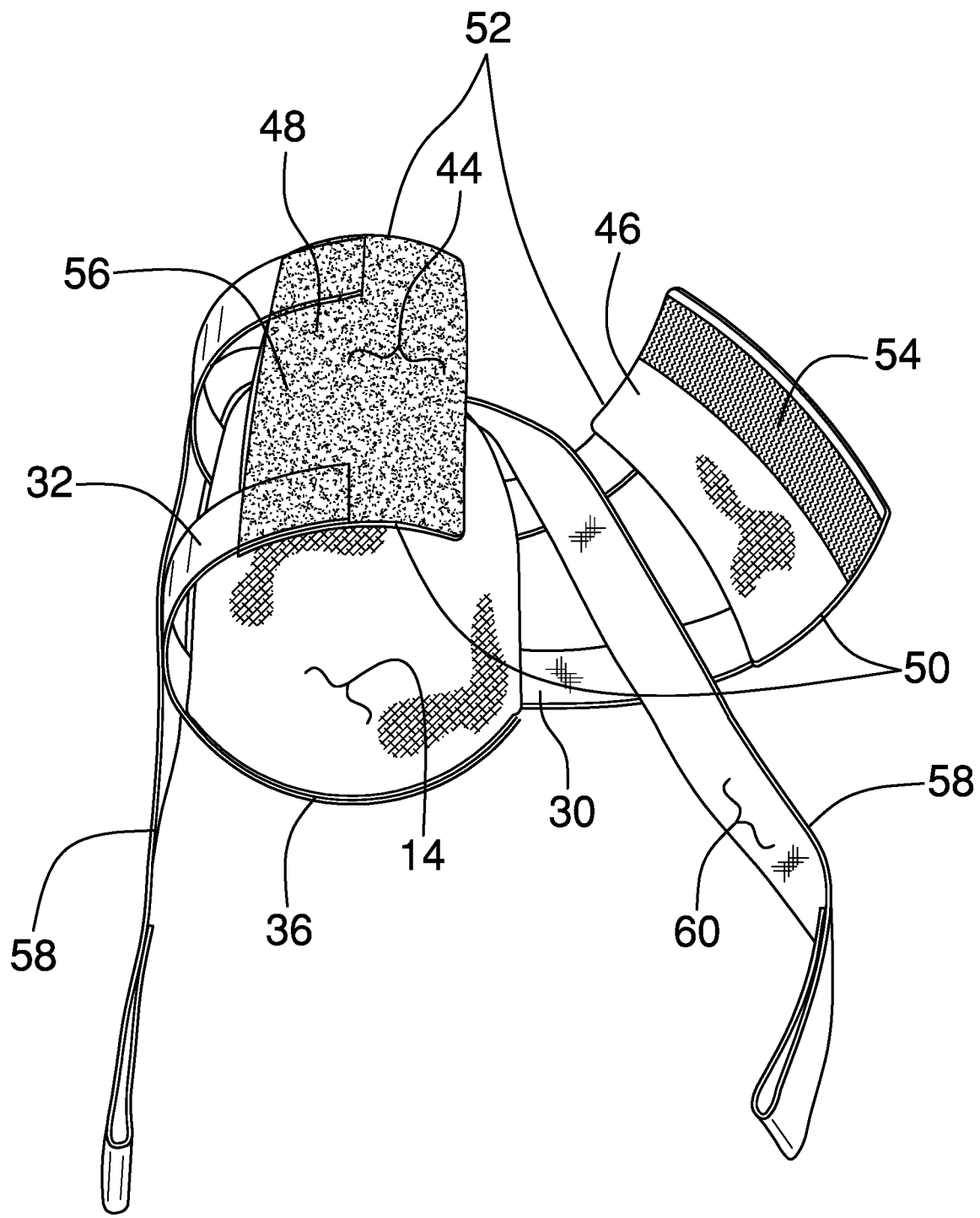
FIG. 2 is an isometric view of an embodiment of the disclosure.
Figure 3:
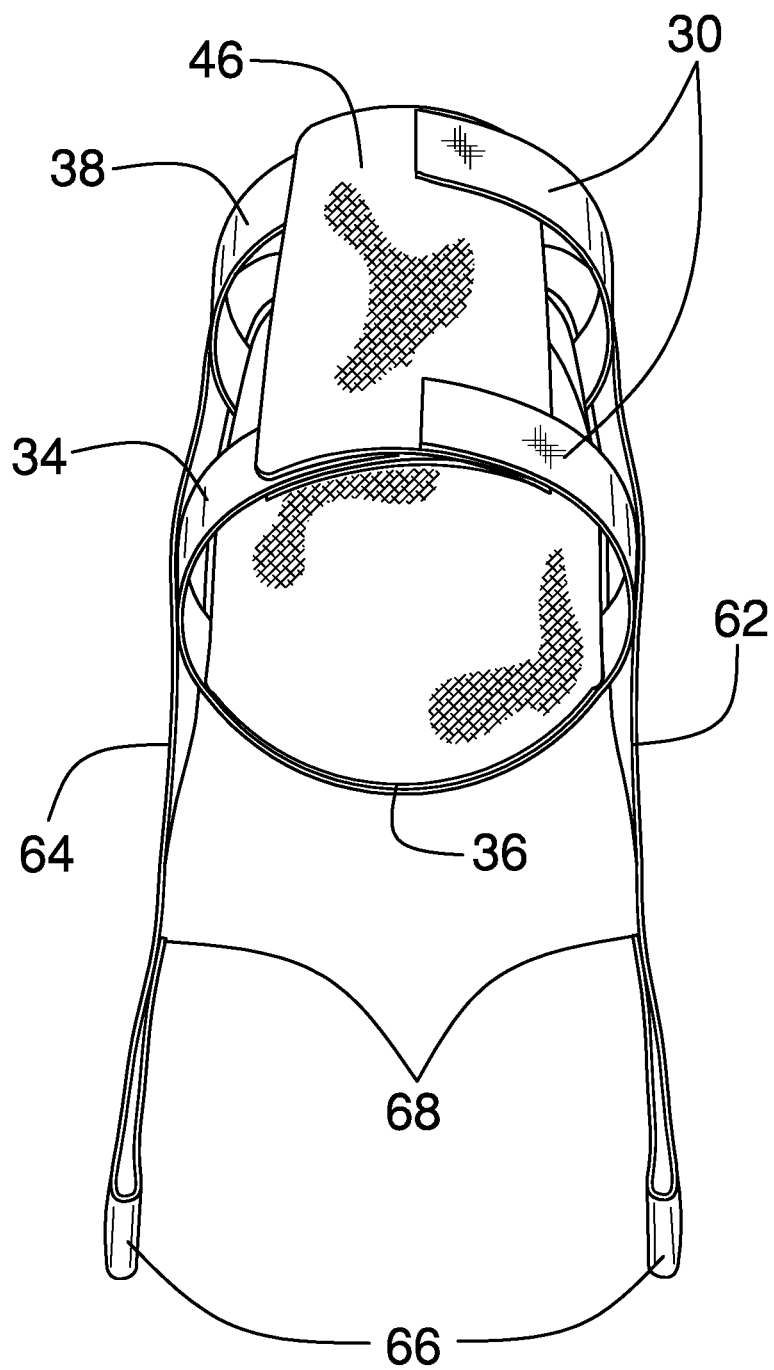
FIG. 3 is an isometric view of an embodiment of the disclosure.
Figure 4:
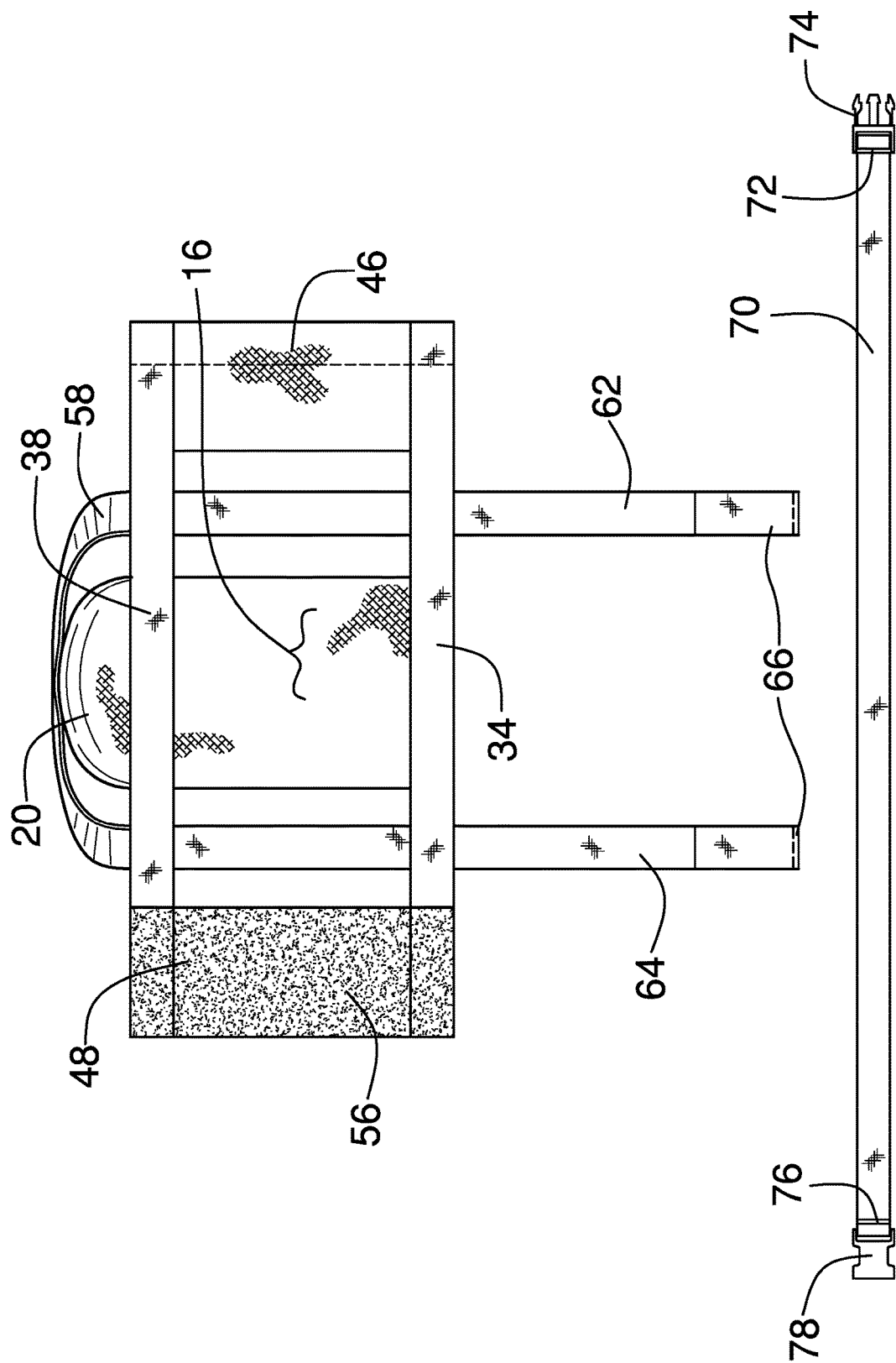
FIG. 4 is a bottom plan view of an embodiment of the disclosure.
Figure 5:
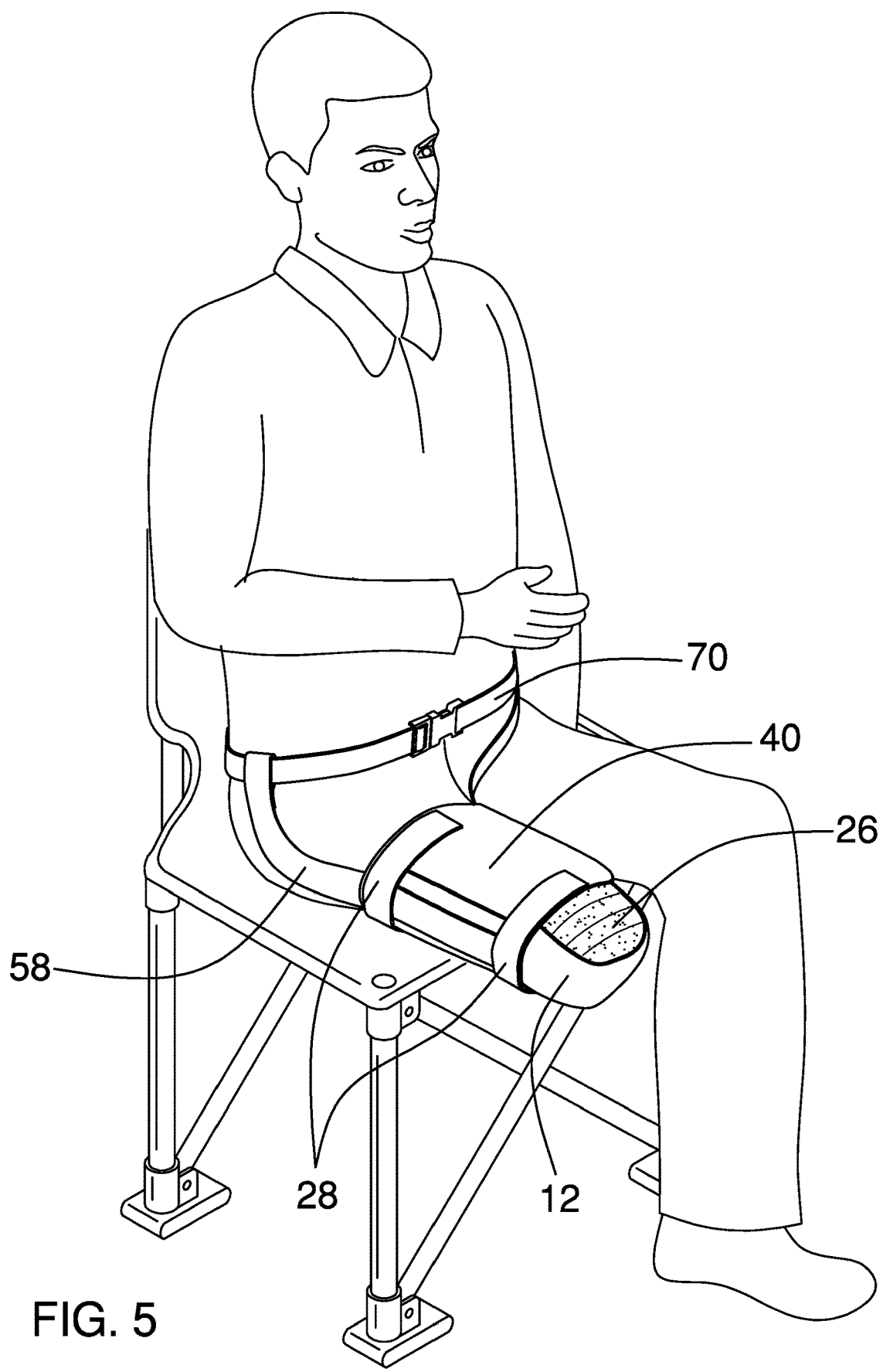
FIG. 5 is an in-use view of an embodiment of the disclosure.

With reference now to the drawings, and in particular to FIGS. 1 through 5 thereof, a new medical wrap embodying the principles and concepts of an embodiment of the disclosure and generally designated by the reference numeral 10 will be described.

As best illustrated in FIGS. 1 through 5, the amputated leg medical wrap apparatus 10 generally comprises a bottom pad 12 having a bottom inner surface 14, a bottom outer surface 16, a back portion 18, a bottom portion 20, a right side portion 22, and a left side portion 24. The bottom pad 12 is cupped such that the bottom portion 20, the right side portion 22, and the left side portion 24 extend upwards from the bottom portion 20 and are configured to cover an underside, a medial side, and a lateral side of a user's amputated leg stump 26. A pair of straps 28 is coupled to the bottom pad 12. Each of the pair of straps 28 is coupled to the bottom outer surface 16 of the back portion and has a right extension 30 and a left extension 32. The pair of straps 28 comprises a top strap 34 coupled adjacent an upper edge 36 of the bottom pad and a bottom strap 38 coupled proximal the bottom portion 20.

A pair of top pads 40 is coupled to the pair of straps 28. The pair of top pads 40 has a top inner surface 42 and a top outer surface 44. The pair of top pads 40 comprises a right top pad 46 and a left top pad 48 coupled to the right extension 30 and the left extension 32, respectively, of the top strap 34 and the bottom strap 38. The top strap 34 and the bottom strap 38 are coupled adjacent a top edge 50 and a bottom edge 52 of the pair of top pads 40, respectively. The right top pad 46 has a first hook-and-loop fastener 54 coupled to the top inner surface 42 and the left top pad 48 has a second hook-and-loop fastener 56 coupled to the top outer surface 44. The first 54 and second hook-and-loop fasteners 56 are selectively engageable and configured to secure the apparatus 10 to the user's amputated leg stump 26. The first hook-and-loop fastener 54 may be a strip occupying 20%-30% of the top inner surface 42 of the right top pad 46 and adjacent an outer edge 56 of the right top pad. The second hook-and-loop fastener 56 is continuously disposed on the entire top outer surface 44 of the left top pad 48. The first hook-and-loop fastener 54 may thus be adjustably coupled to different portions of the second hook-and-loop fastener 56.

A belt strap 58 has a belt strap inner surface 60 coupled to the bottom outer surface 16 of the bottom portion 20 and comprises a right belt strap extension 62 and a left belt strap extension 64 each having a looped top end 66 extending past the upper edge 36 of the bottom pad. The looped top end 66 of each of the right belt strap extension 62 and the left belt strap extension 64 is formed by coupling a distal end 68 of each of the right belt strap extension 62 and the left belt strap extension 64 to the belt strap inner surface 60. The looped top end 66 of each of the right belt strap extension and the left belt strap extension is configured to receive a standard belt or may be used with a designated waist belt 70. The waist belt 70 has a right end 72 having a buckle 74 and a left end 76 having a clasp 78. The buckle 74 and the clasp 76 are selectively engageable.

In use, the waist belt 70 is threaded through the looped top end 66 of each of the right belt strap extension 62 and the left belt strap extension 64. The buckle 74 and the clasp 76 are selectively engaged to secure the waist belt 70 around a user's waist. The bottom pad 12 is positioned in place and the pair of top pads 40 are engaged to secure the apparatus 10. The belt strap 58 provides additional support.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

We claim:

1. An amputated leg medical wrap apparatus comprising:
   a bottom pad, the bottom pad having a bottom inner surface, a bottom outer surface, a back portion, a bottom portion, a right side portion, and a left side portion;
   a pair of straps coupled to the bottom pad, each of the pair of straps being coupled to the bottom outer surface and having a right extension and a left extension, the pair of straps comprising a top strap and a bottom strap;
   a pair of top pads coupled to the pair of straps, the pair of top pads having a top inner surface and a top outer surface, the pair of top pads comprising a right top pad and a left top pad coupled to the right extension and the left extension, respectively, of the top strap and the bottom strap, the right top pad having a first hook-and-loop fastener coupled to the top inner surface and the left top pad having a second hook-and-loop fastener coupled to the top outer surface, the first and second hook-and-loop fasteners being selectively engageable and configured to secure the apparatus to a user's amputated leg stump; and
   a belt strap coupled to the bottom pad, the belt strap being coupled to the bottom outer surface and comprising a right belt strap extension and a left belt strap extension each having a looped top end extending past an upper edge of the bottom pad, the looped top end of each of the right belt strap extension and the left belt strap extension being configured to receive a waist belt.

2. The amputated leg medical wrap apparatus of claim 1 further comprising the bottom pad being cupped such that the bottom portion, the right side portion, and the left side portion extend upwards from the bottom portion and are configured to cover an underside, a medial side, and a lateral side of the user's amputated leg stump.

3. The amputated leg medical wrap apparatus of claim 1 further comprising the first hook-and-loop fastener being a strip occupying 20%-30% of the top inner surface of the right top pad and adjacent an outer edge of the right top pad, the second hook-and-loop fastener being continuously disposed on the entire top outer surface of the left top pad.

4. The amputated leg medical wrap apparatus of claim 1 further comprising the pair of straps being coupled to the back portion, the right side portion, and the left side portion, the top strap being coupled adjacent the upper edge of the bottom pad and the bottom strap being coupled proximal the bottom portion.

5. The amputated leg medical wrap apparatus of claim 4 further comprising the top strap and the bottom strap being coupled adjacent a top edge and a bottom edge of the pair of top pads, respectively.

6. The amputated leg medical wrap apparatus of claim 1 further comprising the belt strap being coupled to the bottom portion of the bottom pad.

7. The amputated leg medical wrap apparatus of claim 1 further comprising a belt strap inner surface being coupled to the bottom pad, the looped top end of each of the right belt strap extension and the left belt strap extension being formed by coupling a distal end of each of the right belt strap extension and the left belt strap extension to the belt strap inner surface.

8. An amputated leg medical wrap apparatus comprising:
   a bottom pad, the bottom pad having a bottom inner surface, a bottom outer surface, a back portion, a bottom portion, a right side portion, and a left side portion, the bottom pad being cupped such that the bottom portion, the right side portion, and the left side portion extend upwards from the bottom portion and are configured to cover an underside, a medial side, and a lateral side of a user's amputated leg stump;
   a pair of straps coupled to the bottom pad, each of the pair of straps being coupled to the bottom outer surface of the back portion and having a right extension and a left extension, the pair of straps comprising a top strap coupled adjacent an upper edge of the bottom pad and a bottom strap coupled proximal the bottom portion;

a pair of top pads coupled to the pair of straps, the pair of top pads having a top inner surface and a top outer surface, the pair of top pads comprising a right top pad and a left top pad coupled to the right extension and the left extension, respectively, of the top strap and the bottom strap, the top strap and the bottom strap being coupled adjacent a top edge and a bottom edge of the pair of top pads, respectively, the right top pad having a first hook-and-loop fastener coupled to the top inner surface and the left top pad having a second hook-and-loop fastener coupled to the top outer surface, the first and second hook-and-loop fasteners being selectively engageable and configured to secure the apparatus to the user's amputated leg stump, the first hook-and-loop fastener being a strip occupying 20%-30% of the top inner surface of the right top pad and adjacent an outer edge of the right top pad, the second hook-and-loop fastener being continuously disposed on the entire top outer surface of the left top pad; and a belt strap coupled to the bottom pad, the belt strap having a belt strap inner surface coupled to the bottom outer surface of the bottom portion and comprising a right belt strap extension and a left belt strap extension each having a looped top end extending past the upper edge of the bottom pad, the looped top end of each of the right belt strap extension and the left belt strap extension being formed by coupling a distal end of each of the right belt strap extension and the left belt strap extension to the belt strap inner surface, the looped top end of each of the right belt strap extension and the left belt strap extension being configured to receive a waist belt.

9. A belt and amputated leg medical wrap apparatus combination comprising:

a waist belt, the waist belt having a right end having a buckle and a left end having a clasp, the buckle and the clasp being selectively engageable to secure the waist belt around a user's waist;

a bottom pad, the bottom pad having a bottom inner surface, a bottom outer surface, a back portion, a bottom portion, a right side portion, and a left side portion, the bottom pad being cupped such that the bottom portion, the right side portion, and the left side portion extend upwards from the bottom portion and are configured to cover an underside, a medial side, and a lateral side of a user's amputated leg stump;

a pair of straps coupled to the bottom pad, each of the pair of straps being coupled to the bottom outer surface of the back portion and having a right extension and a left extension, the pair of straps comprising a top strap coupled adjacent an upper edge of the bottom pad and a bottom strap coupled proximal the bottom portion;

a pair of top pads coupled to the pair of straps, the pair of top pads having a top inner surface and a top outer surface, the pair of top pads comprising a right top pad and a left top pad coupled to the right extension and the left extension, respectively, of the top strap and the bottom strap, the top strap and the bottom strap being coupled adjacent a top edge and a bottom edge of the pair of top pads, respectively, the right top pad having a first hook-and-loop fastener coupled to the top inner surface and the left top pad having a second hook-and-loop fastener coupled to the top outer surface, the first and second hook-and-loop fasteners being selectively engageable and configured to secure the apparatus to the user's amputated leg stump, the first hook-and-loop fastener being a strip occupying 20%-30% of the top inner surface of the right top pad and adjacent an outer edge of the right top pad, the second hook-and-loop fastener being continuously disposed on the entire top outer surface of the left top pad; and a belt strap coupled to the bottom pad, the belt strap having a belt strap inner surface coupled to the bottom outer surface of the bottom portion and comprising a right belt strap extension and a left belt strap extension each having a looped top end extending past the upper edge of the bottom pad, the looped top end of each of the right belt strap extension and the left belt strap extension being formed by coupling a distal end of each of the right belt strap extension and the left belt strap extension to the belt strap inner surface, the looped top end of each of the right belt strap extension and the left belt strap extension receiving the waist belt.

* * * * *